US009387041B2

(12) United States Patent
Dahotre et al.

(10) Patent No.: US 9,387,041 B2
(45) Date of Patent: Jul. 12, 2016

(54) LASER-ASSISTED MACHINING (LAM) OF HARD TISSUES AND BONES

(71) Applicant: University of North Texas, Denton, TX (US)

(72) Inventors: Narendra B. Dahotre, Denton, TX (US); Soundarapandian Santhanakrishnan, Tamilnadu (IN)

(73) Assignee: University of North Texas, Denton, TX (US)

( * ) Notice: Subject to any disclaimer, the term of this patent is extended or adjusted under 35 U.S.C. 154(b) by 312 days.

(21) Appl. No.: 14/216,966

(22) Filed: Mar. 17, 2014

(65) Prior Publication Data

US 2014/0263214 A1 Sep. 18, 2014

Related U.S. Application Data

(60) Provisional application No. 61/792,341, filed on Mar. 15, 2013.

(51) Int. Cl.
| | |
|---|---|
| *B23K 26/00* | (2014.01) |
| *B23K 26/36* | (2014.01) |
| *G06F 19/00* | (2011.01) |
| *A61B 17/16* | (2006.01) |
| *A61B 18/20* | (2006.01) |

(52) U.S. Cl.
CPC .............. *A61B 18/203* (2013.01); *B23K 26/00* (2013.01); *B23K 26/36* (2013.01); *G06F 19/00* (2013.01); *A61B 18/201* (2013.01)

(58) Field of Classification Search
CPC ........ A61B 17/16; B23K 26/00; B23K 26/36; G06F 19/00

USPC ............ 219/121.61, 121.62, 121.67–121.72; 700/166; 250/492.1
See application file for complete search history.

(56) References Cited

U.S. PATENT DOCUMENTS

| | | | | |
|---|---|---|---|---|
| 5,415,652 A | * | 5/1995 | Mueller ............... | A61C 1/0046 604/27 |
| 2007/0062920 A1 | | 3/2007 | Shin | |
| 2008/0153067 A1 | | 6/2008 | Berckmans et al. | |
| 2009/0130622 A1 | * | 5/2009 | Bollinger ............. | A61C 1/0046 433/29 |
| 2010/0243625 A1 | * | 9/2010 | Osako .................. | B23K 26/38 219/121.72 |

(Continued)

FOREIGN PATENT DOCUMENTS

WO 99/55243 11/1999

OTHER PUBLICATIONS

S. Santhanakrishnan, Y. H. Ho, and N. B. Dahotre, Laser coating of hydroxyapatite on Mg for enhanced physiological corrosion resistance and biodegradability, Materials Technology (2012) 1-5.

(Continued)

*Primary Examiner* — Samuel M Heinrich
(74) *Attorney, Agent, or Firm* — Jackson Walker, LLP

(57) ABSTRACT

An apparatus and method for laser-assisted machining (LAM) of bone without raising the temperature of the surrounding bone is discussed. The method of LAM of bone involves determining a target bone needing to be machined an then scanning a high power density laser beam along the bone at a machining rate that produces low-heat affected zones (HAZ) on the target bone. The process and apparatus is advantageous over conventional technologies because it provides a chemically clean, coherent, and monochromatic beam to the region to be machined.

18 Claims, 12 Drawing Sheets

(56) References Cited

U.S. PATENT DOCUMENTS

| | | |
|---|---|---|
| 2011/0218524 A1 | 9/2011 | Cattaneo |
| 2011/0319879 A1 | 12/2011 | Shimokita et al. |
| 2013/0134141 A1 | 5/2013 | Santner et al. |

OTHER PUBLICATIONS

J. P. Winkler, The temperature study of laser-irradiated bone, Dissertation for Doctor of Philosophy, The University of Tennessee, Knoxville, TN (1997) 1-86.

K. J. Altman, Microscale machining and mechanical characterization of bone tissue, Thesis for Master of Science, The Ohio State University, Columbus, OH (2009) 1-105.

M. Ivanenko, M. Werner, S. Afilal, M. Klasing, P. Hering, Ablation of bone tissue with pulsed CO2 lasers, Medical Laser Application 20 (2005) 13-23.

A. B. Imhoff, The use of lasers in orthopaedic surgery, Operative Techniques in Orthopaedics 5 (1995) 192-203.

J. Burgner, M. Mueller, Robot assisted laser bone processing: Marking and cutting experiments, International Conference on Advanced Robotics (ICAR 2009), Jun. 22-26, 2009, 1-6.

J. M. White, D. Gekelman, J. Budd, Lasers and dental soft tissues: Reflections on our years of research, International Congress Series 1248 (2003) 13-19.

R. J. Wallace, C. J. Whitters, J. A. McGeough, A. Muir, Experimental evaluation of laser cutting of bone, Journal of Materials Processing Technology 149 (2004) 557-1560.

J. L. Fox, The use of laser radiation as a surgical "light knife," Journal of Surgical Research 9 (1969) 199-205.

J. D. B. Featherstone, D. Fried, Fundamental interactions of lasers with dental hard tissues, Medical Laser Application 16 (2001) 181-194.

F. W. Neukam, F. Stelzle, Laser tumor treatment in oral and maxillofacial surgery, Physics Procedia 5 (2010) 91-100.

B. L. Yilbas, Z. Yilbas, M. Sami, Thermal processes taking place in the bone during CO2laser irradiation, Optics & Laser Technology 28 (1996) 513-519.

S. Karmani, The thermal properties of bone and the effects of surgical intervention, Current Orthopaedics 20 (2006), 52-58.

L. Cangueiro, et al, Femtosecond Laser Ablation of Bovine Cortical Bone, J. Biomed. Opt. 17(12) Dec. 4, 2012.

R.J. Wallace, et al, Experimental Evaluation of Laser Cutting of Bone, J. Materials Processing Technology, 149 (2004), 557-560.

* cited by examiner

Table 1. Governing equations for computational model of laser-assisted bone machining process.

| # | Boundary conditions | Equation | Eq # |
|---|---|---|---|
| Whole geometry | Governing equation | $\rho c_p \left[\frac{\partial T}{\partial t}\right] = k \left[\left(\frac{\partial^2 T}{\partial x^2}\right) + \left(\frac{\partial^2 T}{\partial y^2}\right)\right]$ | (1) |
| 6 | Heat flux, natural convection cooling and radiation | $-k\frac{\partial T}{\partial y} = \varphi P_g - h[T - T_i]$ $- \varepsilon\sigma[T^4 - T_i^4]$ where, $\varphi = 1$ for $0 \leq t \leq t_r$, and $\varphi = 0$ for $t \geq t_r$ | (2) |
| | Average laser power density in Gaussian distribution | $P_g = A \left[\frac{P}{\left(\frac{\pi}{4}D^2\right)}\right] \cdot \exp\left[-\left(\frac{(x - x_r)^2}{2\phi^2}\right)\right]$ | (3) |
| 1,9 | Natural convection cooling and radiation | $-k\frac{\partial T}{\partial x} = h[T - T_i] - \varepsilon\sigma[T^4 - T_i^4]$ | (4) |
| 3,8 | Natural convection cooling and radiation | $-k\frac{\partial T}{\partial y} = h[T - T_i] - \varepsilon\sigma[T^4 - T_i^4]$ | (5) |
| 2 | Insulation | $\frac{\partial T}{\partial y} = 0$ | (6) |

Figure 2A

Table 2. Laser-assisted machining parameters and machined attributes.

| Ex # | Laser power (W) | Scanning speed (m/s) | Residence time (ms)* | Laser Energy Density (×10⁶ J/m²)** | Laser Machining Attributes | | | | | Machining Rate*** (m³/s/W) Or (m⁵/J) ×10⁻² |
|---|---|---|---|---|---|---|---|---|---|---|
| | | | | | Measured Experimentally | | Determined Computationally | | Machining Rate (m³/s) | |
| | | | | | Depth (μm) | Width (μm) | Depth (μm) | Width (μm) | | |
| 1 | 300 | 0.2 | 3.0 | 3.18 | 140 | 300 | 105 | 265 | 3.3 | 1.1 |
| 2 | 400 | 0.2 | 3.0 | 4.24 | 190 | 360 | 185 | 330 | 6.4 | 1.6 |
| 3 | 550 | 0.25 | 2.4 | 4.67 | 250 | 410 | 225 | 375 | 14.4 | 2.6 |
| 4 | 500 | 0.2 | 3.0 | 5.31 | 330 | 470 | 295 | 430 | 19.1 | 3.8 |
| 5 | 450 | 0.15 | 4.0 | 6.36 | 410 | 530 | 430 | 535 | 22.6 | 5.0 |
| 6 | 600 | 0.2 | 3.0 | 6.40 | 430 | 540 | 445 | 550 | 32.8 | 5.5 |
| 7 | 700 | 0.2 | 3.0 | 7.43 | 590 | 650 | 610 | 690 | 65.2 | 9.3 |
| 8 | 400 | 0.1 | 6.0 | 8.49 | 730 | 800 | 780 | 810 | 61.1 | 15.3 |

\* Residence time (s) = Laser beam diameter (m)/scanning speed (m/s))
\*\* Laser energy density (J/m²) = (Laser power (J/s)/laser irradiation area (m²)) × (laser beam diameter (m)/scanning speed (m/s))
\*\*\* Machining rate (m⁵/Js) = Volume of material removed (m³)/residence time (s)/laser energy density (J/m²)

Figure 3A

Table 3. Lasers for use with laser-assisted bone machining systems.

| Type of laser | Wavelength (nm) | Power (W) | Beam diameter (μm) | Energy density (J/cm²) | Depth of cutting (μm) | Ref |
|---|---|---|---|---|---|---|
| Ti-sapphire | 775 | $1–15 \times 10^{-3}$ | 6 | 9–14 | 10–100 | Altman, 2009 |
| CO$_2$ | 9600–10600 | ------ | 300–1100 | 75–85 | 150–1000 | Ivanenko, 2005 |
| Excimer | 305 | ------ | ------ | 2–10 | 1–20 | Imhoff, 1995 |
| YAG | 2100 | ------ | ------ | 30–120 | 20–120 | Imhoff, 1995 |

Figure 7

LASER-ASSISTED MACHINING (LAM) OF HARD TISSUES AND BONES

RELATED APPLICATIONS

This application claims the benefit of U.S. Provisional Patent Application Ser. No. 61/792,341, entitled LASER-ASSISTED MACHINING (LAM) OF HARD TISSUES AND BONES, filed on Mar. 15, 2013, the entire content of which is hereby incorporated by reference.

FEDERALLY FUNDED RESEARCH

No federal funds were used in the development of the present invention.

JOINT RESEARCH AGREEMENTS

Not applicable.

SEQUENCE LISTINGS

Not applicable.

BACKGROUND

The present invention relates generally to a system and methods of machining hard tissues, such as bone, and more specifically to a system for the process and apparatus for laser assisted machining ("LAM") of bone tissue.

Bone tissue is a type of dense connective tissue that is found in a variety complex internal and external structure. They are lightweight yet strong and hard to serve multiple functions. These rigid organs constitute part of the endoskeleton of vertebrates commonly known to protect the various soft organs of the body. In spite of their rigidity, bones are very active tissues that produce red and white blood cells and store minerals. Bones are made of a multiphase matrix of both organic minerals (i.e. collagen) and inorganic substances (i.e. hydroxyapatite). When bones are damaged, they usually heal quickly. However, in the case of a complicated breaks and deterioration due to (car) accidents and diseases (cancers) and the like, the damaged hard bone tissue must undergo replacement surgery, or bone graph.

One embodiment of the current invention can be used for machining bone tissue for surgical grafting. Bone grafting is a surgical procedure that replaces missing bone in order to repair extremely complex bone fractures, or to repairs that pose a significant health risk due to disease (cancer) to the patient. However, in order for bones to regenerate they require a very small fracture space or some type of scaffold to do so. Bone grafts may be autologous (bone harvested from the patient's own body, often from the iliac crest), allograft (cadaveric bone usually obtained from a bone bank), or synthetic (often made of hydroxyapatite or other naturally occurring and biocompatible substances) with similar mechanical properties to bone. Most bone grafts are expected to be reabsorbed and replaced as the natural bone heals over a few months' time.

The principals involved in successful bone grafts include osteoconduction (guiding the reparative growth of the natural bone), osteoinduction (encouraging undifferentiated cells to become active osteoblasts), and osteogenesis (living bone cells in the graft material contribute to bone remodeling), wherein it is understood that osteogenesis only occurs with autografts.

Another situation where bone tissue replacement and/or repair is necessary is total joint replacement such as knee, hip, shoulder, elbow, etc. Wherein often the entire damageged/diseased/malfunctioning bone tissues of the joint and partial bone tissues surrounding the joint are removed and replaced with an artificial inorganic (metallic/ceramic/polymeric) joint that is also grafted/integrated with the surrounding bone tissues.

The precision of particular surgical tools used for machining bone for the purpose of bone grafting and replacement is determined in part by the size and workspace of tools used. Conventional bone machining techniques include slicing, sawing, cutting, drilling, coring, milling, and grinding, with tools such as drills, saws, hammers, chisels, and grinders. These conventional techniques present significant limitations, such as high mechanical loading, high friction, and poor accuracy. Additionally, these conventional techniques are also slow, and usually cause damage to surrounding tissues, which may result in long recovery and healing times.

In contrast to conventional tool listed above, the minimum width of a laser beam is the width of a beam of light. As such, one advantages of doing surgeries using lasers instead of scalpel blades has resulted in less pain, less swelling and less bleeding for a majority of patients. As a laser beam can cut through tissues to seals blood vessels resulting in minimal bleeding. Lasers can also seal lymphatic vessels minimizing postoperative swelling, and it seals nerve ending reducing post-surgical pain. The fact that only the laser beam (not an instrument) touches the touches the tissues (without any mechanical loading) eliminates much of the trauma that occurs using standard surgical techniques.

No successive laser technology has been reported to match a bone graft with the section of hard tissue (bone) that has been surgically removed due to disease/decay/damage. Moreover, the invention described herein can cut, drill, or shape the remaining healthy portion for integration with a bone graph or external biomaterial implant.

In order to effectively and efficiently machine a living bone work piece, without causing heat damage through overheating from mechanical loading and friction of the cutting tool, the present invention provides a novel system involving apparatus and process for laser-assisted bone machining that provides narrow beams with high power density, and creates little or no heat-affected zone ("HAZ"), thereby avoiding the difficulties experienced with conventional bone machining techniques.

SUMMARY

The present invention provides a system involving a process and apparatus for laser-assisted machining (LAM) of bone. The currently-disclosed system is advantageous over conventional technologies, in part because it provides a chemically clean, coherent, and monochromatic beam to the region to be machined without physical contact and mechanical loading. The invention provides a narrow beam with a high power density, and little or no heat affected zone ("HAZ").

A first embodiment of the current invention is a method of laser-assisted machining of a bone. The method includes a first step of determining a bone target volume or target area to be machined. Once the bone target volume has been determined, a focused laser beam will be used to scan the laser along a surface area axis of the bone's target volume at a calculated machining-rate. The focused laser beam with a Gaussian laser beam profile will generate intense heat, which will instantaneously evaporate the liquid layer and other organic (collagen) and inorganic (hydroxyapatite) components of the bone thereby ejecting a bone residue from the predetermined target bone volume creating a machined void in the bone. The machining rate of the bone is determined from calculations using parameters such as: laser power output; the target bone volume; the diameter of the focused laser beam; the laser scanning speed; and the residence time. The laser energy density provides a narrow laser beam with a high power density with little or no heat affected zones ("HAZ") on the bone targeted volume. The method utilizes a Gaussian shaped or top-hat laser beam profile for the bone target. In a preferred embodiment the choice of lasers used can be selected from those that generate the focused laser beam having the laser energy density in the range of 2.0 to $12.0 \times 10^6$ J/Additionally, the focused laser beam should have a wavelength in the range of 300 nm to 10,600 nm. Lasers can be chosen from: a Ti-Sapphire laser; a $CO_2$ laser; a Excimer laser; or a YAG laser. In a third preferred embodiment, the laser is a diode-pumped ytterbium (PG-YLS-3000) continuous wave fiber laser having a 1,060-1,079 nm wavelength with a Gaussian beam of focal spot of 0.3 mm diameter used at a fixed stand-off distance of 315 mm from the surface area axis.

In a second preferred embodiment, a vision system (i.e. ScanLab) and a computer numeric controlled ("CNC") robotic system are integrated with the laser for full automation of selecting the bone target volume and scanning the focused laser beam along a surface area axis of bone target volume at a machining rate. A fifth preferred embodiment sets the residence time of the laser to be in the range of 2-4 ms, wherein the focused laser beam generates a heat intensity in the range of $4.2-9.9 \times 10^7$ W/m².

In a third embodiment, the present invention includes an apparatus for laser-assisted bone machining, comprising: a) a laser; b) a personal computer; c) an RTC; d) a beam expander; e) a dynamic focusing unit, such as a varioSCAN®; f) a power supply; g) a scan head; and h) an objective.

A fourth embodiment of the present invention comprises a process for laser-assisted machining of bone. This process includes the steps of a) observing a region of bone to be machined; b) calculating the temperature-dependent material properties of the region of bone; c) determining parameters for laser-assisted machining based on the temperature-dependent material properties of the region of bone; and d) performing laser-assisted bone machining using the determined parameters.

A fifth embodiment of the present invention is an apparatus for machining bone, comprising: a) a laser source capable of delivering a focused laser beam with a Gaussian laser beam profile or top-hat beam profile; b) a dynamic focusing unit for delivering the focused laser beam to a visualized target site; c) a real time controller ("RTC") capable of simultaneous processing of visualized target site data and controlling the laser source and controlling the dynamic focusing unit, wherein the RTC is able to correct laser source output for the purpose of preventing heat affected zones in the bone target and machining bone in a predetermined pattern. A first preferred embodiment includes a laser source delivers a beam having a 1060-1079 nm wavelength with a Gaussian or top-hat beam of focal spot of 0.3 mm diameter. A second preferred embodiment includes a laser having a diode-pumped ytterbium (PG-YLS-3000) continuous wave fiber laser having a 1060-1079 nm wavelength with a Gaussian beam of focal spot of 0.3 mm diameter used at a fixed stand-off distance of 315 mm from the surface area axis. A third preferred embodiment is a focused laser beam has a laser energy density in the range of 2.0 to $12.0 \times 10^6$ J/m², and the laser beam has a wavelength in the range of 300 nm to 10,600 nm. The preferred laser can be selected from a Ti-Sapphire laser, a $CO_2$ laser, a Excimer laser, or a YAG laser. Additionally, a computer numeric controlled ("CNC") robotic system is preferred in order to enable the laser to have full automation of selecting a target bone volume and scanning the focused laser beam along a surface area axis at a determined machining rate. A fourth preferred embodiment is a laser having a resident time in the range of 2-4 ms when the focused laser beam is generating a heat intensity in the range of $4.2-9.9 \times 10^7$ W/m².

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 2A shows the governing equations for computational model used in the present invention to represent the temperature-dependent material properties of a region of bone.

FIG. 3A shows a table of bone tissue machining rate as a function of laser energy density for the experiments carried out according to the present invention.

FIG. 7 shows a table of lasers for use with laser-assisted bone machining systems of the current invention.

DETAILED DESCRIPTION

Figure 1A:
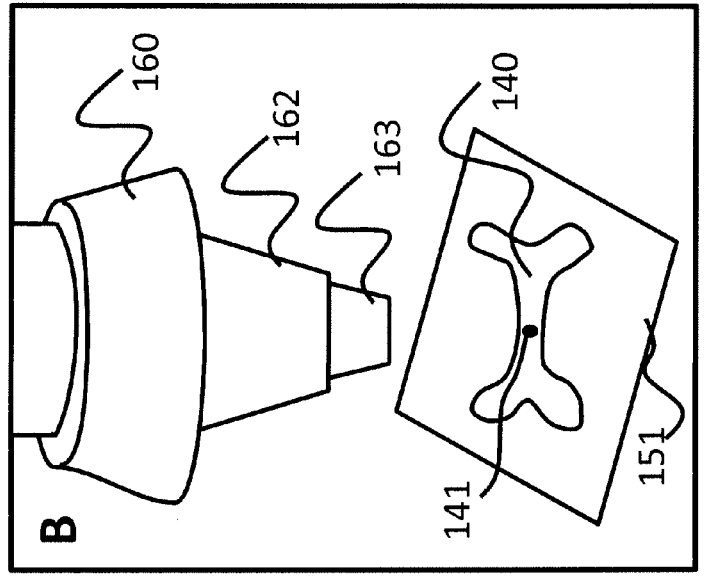
FIG. 1A (Panel A) shows an illustration of laser system for laser-assisted bone machining. (Panel B) shows an enlarged illustration of a bone sample undergoing machining.
Figure 1A:
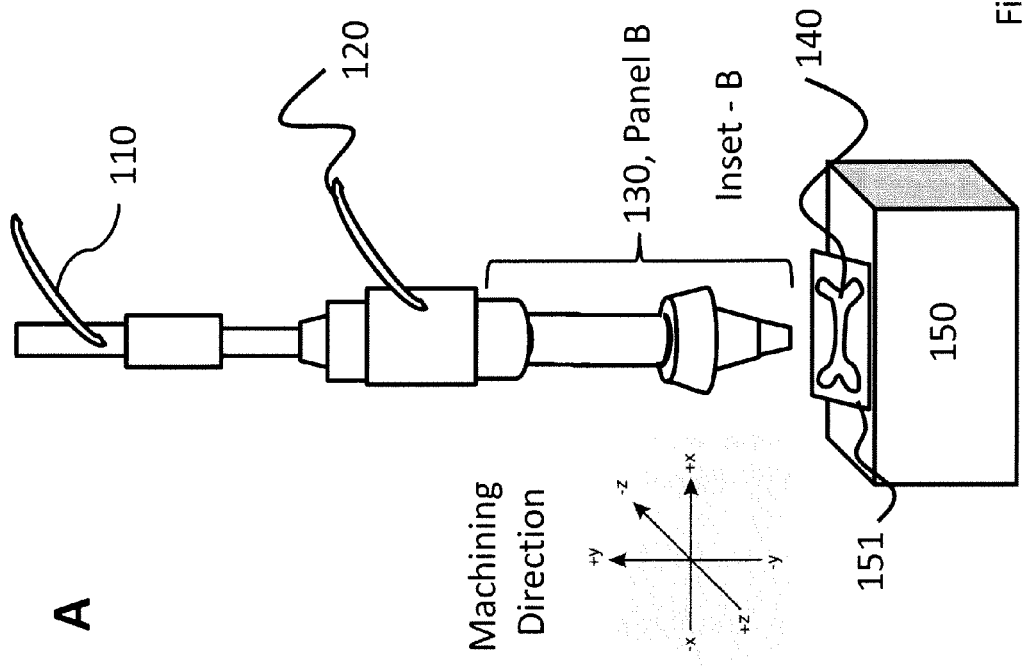
Figure 1B:
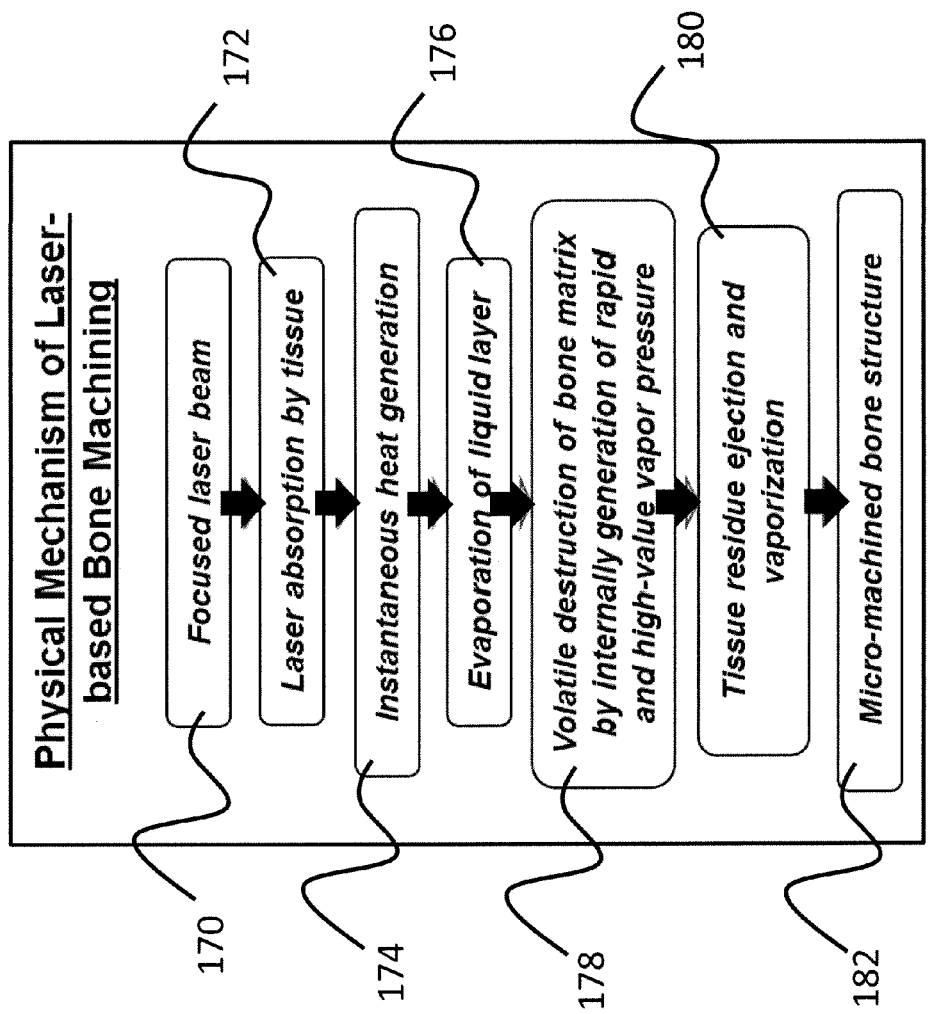
FIG. 1B shows the sequential physical mechanisms of laser based bone machining.

Terms: Before describing the present invention in detail, it is to be understood that this invention is not limited to particular compositions or composition delivery systems, which may vary. One having ordinary skill in the art will understand that the terminology used herein is for the purpose of describing particular embodiments only, and is not intended to be limiting. In addition, before describing detailed embodiments of the invention, it will be useful to set forth definitions that are used in describing the invention. The definitions set forth apply only to the terms as they are used in this patent and may not be applicable to the same terms as used elsewhere, for example in scientific literature or other patents or applications including other applications by these inventors or assigned to common owners. Additionally, when examples are given, they are intended to be exemplary only and not to be restrictive. In describing and claiming the present invention, the following terminology will be used in accordance with the definitions set out below.

It must be noted that, as used in this specification and the appended claims, the singular forms "a," "an" and "the" include plural referents unless the context clearly dictates otherwise. Thus, for example, reference to "a pharmacologically active agent" includes a mixture of two or more such compounds, reference to "a base" includes mixtures of two or more bases, reference to "an acid" includes mixtures of two or more acids, and the like.

The term "Autologous (or autogenous) bone grafting" as used herein refers to and involves utilizing bone obtained from the same individual receiving the graft. Bone can be harvested from non-essential bones, such as from the iliac crest, or more commonly in oral and maxillofacial surgery, from the mandibular symphysis (chin area) or anterior mandibular ramus (the coronoid process); this is particularly true for block grafts, in which a small block of bone is placed whole in the area being grafted. When a block graft are performed, autogenous bone is the most preferred because there is less risk of the graft rejection because the graft originated from the patient's own body. A negative aspect of autologous grafts is that an additional surgical site is required, in effect adding another potential location for post-operative pain and complications. Autologous bone is typically harvested from intra-oral sources as the chin or extra-oral sources as the iliac crest, the fibula, the ribs, the mandible and even parts of the skull.

The term "fiber optic cable" as used herein refers to a cable containing one or more optical fibers that are used to carry light. The optical fiber elements are typically individually coated with plastic layers and contained in a protective tube suitable for the environment where the cable will be deployed.

The term "protective gas" as used herein refers to an inert gas for sample protection. Although nitrogen is not inert a line using 30 liter/min with 35 psi pressure was used as an inert gas protection for the bone sample from burning/charring at elevated temperature.

The term "Gaussian laser beam profile" as used herein refers to a beam of electromagnetic radiation whose transverse electric field and intensity (irradiance) distributions are well approximated by Gaussian functions.

The term "top hat laser beam profile" as used herein refers to a beam of electromagnetic radiation whose transverse electric field and intensity (irradiance) distributions are constant and uniform over the cross section of the beam.

The term "bone" as used herein refers to rigid organs that constitute part of the endoskeleton of vertebrates. They support and protect the various organs of the body, produce red and white blood cells and store minerals. Bone tissue is a type of dense connective tissue. Bones come in a variety of shapes and have a complex internal and external structure, are lightweight yet strong and hard, and serve multiple functions. Bones may also be considered for this invention to be synthetic bones or bone replacement material, including metals and ceramics.

The term "laser energy density" as used herein refers to a parameter of LAM calculated as follows: Laser energy density $(J/m^2)$=(Laser power (J/s)/laser irradiation area $(m^2)$)× (laser beam diameter (m)/scanning speed (m/s)).

The term "bone tissue machining rate" as used herein refers to a machining rate $(m^5/Js)$=Volume of material removed $(m^3)$/residence time (s)/laser energy density $(J/m^2)$ The term "Real time clock controller" (RTC-controller) provide synchronous, interference-resistant control of scan systems and lasers in real time. A signal processor and dynamic link libraries ("DLL") can simplify programming. Alternatively, software from various third-party vendors is also available for handling standard applications. For example, instructions can be loaded in the RTC, processed, and output as 16-bit control signals every 10 µs to the scan system. The RTC-controller can automatically performs vital steps such as micro-vectorization and image field correction. Laser control is synchronized with the scanner movements.

The term "z" as used herein refers to the Z-coordinate in a three dimensional space (m)—(Direction of laser beam motion within the surface plane of substrate)

The term "x" as used herein refers to X-coordinate in a three dimensional space (m)—(Direction normal to the laser beam motion Z, within the surface plane of substrate)

The term "y" as used herein refers to Y-coordinate in a three dimensional space (m)—(Direction normal to both the laser beam motion and the surface plane of substrate, Z and X and along the beam axis)

The term "$\rho$" as used herein refers to Density $(kg/m^3)$

The term "$C_p$" as used herein refers to Specific heat at constant pressure $(J/kg \cdot K)$ The term "T" as used herein refers to Temperature (K, Kelvin)

The term "t" as used herein refers to Time (s, seconds)

The term "K" as used herein refers to Thermal conductivity $(W/m \cdot K)$

The term "$\phi$" as used herein refers to Laser on/off function

The term "$P_g$" as used herein refers to Average laser power density $(W/m^2)$

The term "h" as used herein refers to Heat transfer coefficient $(W/m^2 \cdot K)$ The term "$T_i$" as used herein refers to Initial temperature (K)

The term "$\epsilon$" as used herein refers to Emissivity

The term "$\sigma$" as used herein refers to Stefan-Boltzmann constant $(W/m^2 \cdot K^4)$ The term "Tr" as used herein refers to Laser beam residence time (s)=Diameter of laser beam/Scanning speed The term "A" as used herein refers to Absorptivity of laser beam The term "P" as used herein refers to Laser beam power (W, Watts)

The term "D" as used herein refers to Diameter of laser beam (m, Meters)

The term "$X_r$" as used herein refers to Reference point to represents the center of the laser beam in the geometry along x-axis (m)

The term "$\phi$" as used herein refers to Standard deviation of the Gaussian laser beam (m)

EXAMPLES

The following examples are included to demonstrate preferred embodiments of the invention. It should be appreciated by those of skill in the art that the techniques disclosed in the examples that follow represent techniques discovered by the inventor to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention.

Example 1

Apparatus for Laser-Assisted Machining ("LAM") of Bone

The present invention relates to a system involving a process and apparatus for laser-assisted machining ("LAM") of bone. The LAM provides high precision dimensional machining with minimal or no surrounding tissue damage/trauma. The non-contact, highly-focused laser beam (wavelength in the infrared to ultraviolet range, e.g. 1064 nm wavelength with 300 μm beam diameter) integrated with a robotic-computer controller, offers highly-precision dimensional matching for any complicated structural bones. The afore mentioned technique follows simple procedure and is expected to facilitate rapid recovery without traumatic vibrational related injury, negligible heat-mark and minimal invasive tissue damage that are typically associated with conventional orthopedic techniques and also requiring no blood transfusions. In preliminary efforts the technique of LAM has been successfully tested and it precisely machined the bone depth (140-730 μm) an width (300-800 μm) for different laser energy densities (3-8.5×$10^6$ J/$m^2$)

One embodiment of the present invention provides a laser system for machining hard tissue. The system may comprise a 3 KW diode pumped ytterbium fiber laser, for example, an IPG YLS-3000 laser may be used (IPG Photonics, Oxford, Mass.). An exemplary laser would have a wavelength of 1.07 μm, fiber optics, a scan head (e.g. SCANLAB), a CNC controlled 4-axis motion system, a beam focus diameter of 0.6 mm, and would be operated in continuous wave mode.

An embodiment of the present invention provides a laser system which could be used over a range of energies, for example about 3×$10^6$ J/$m^2$ to about 8.5×$10^6$ J/$m^2$. The laser system can also be used at various speeds, for example about 0.1 m/s to about 0.25 m/s. These parameters impact the depth of melting or vaporization, and the machining rate.

In one embodiment, the present invention comprises an apparatus for laser-assisted bone machining, comprising: a) a laser; b) a personal computer; c) a real time clock/controller (RTC); d) a beam expander; e) a dynamic focusing unit, such as a varioSCAN®; f) a power supply; g) a scan head; and h) an objective.

The dynamic focusing unit (e.g. a varioSCAN® by SCANLAB™) in some embodiments of the invention enables precise, high-performance positioning of the laser focus along the optical axis. In XY scan systems, a dynamic focusing unit can replace costly flat field objectives. Therefore, the dynamic focusing unit is an ideal solution in applications for which standard flat field objectives are unavailable. The dynamic focusing unit can also extend XY scan systems into 3D beam deflection systems. The laser focus is guided along the contour of the workpiece being processed, thus enabling processing in three dimensions. The dynamic focusing unit additionally allows continuously adjusting the image field size, working distance and spot size. Some models of the dynamic focusing unit offer much lower tracking error, resulting in a larger focus-shift range and better spot quality.

The RTC in some embodiments of the invention serves two purposes: 1) keep accurate time/date information; and 2) provide wake up alarms (both during runtime and while sleeping). Since the RTC is externally powered and clocked independently of the processor, it can remain running even when the rest of the system is turned off. An RTC controller card is a mode of communication between a PC and a laser beam scanner, and provides information instantly or with negligible latency.

Turning now to FIG. 1A, which shows a laser system for laser-assisted machining (LAM) of bone includes a laser device. FIG. 1A according to the present invention includes a system having a laser attached electrically and through fiber optics (110). A protective gas line (120) is in fluid communication with the LAM of bone system. A bone sample (140) is shown on a fixture (151) that is on top of a guiding device (150). The laser beam spot (141) is focused on the bone sample (140) using a beam focusing head (130). Panel B shows the laser beam and gas nozzle outlet (160); scale dial for adjusting the protective/cover gas flow (162); and the collar of focusing head (163). The synchronized control of scan systems, lasers and guiding systems is completed using real time controller boards, or computers integrated with each component of the system. In FIG. 1A, the focusing head motion is CNC controlled and integrated with the robotic motion system allowing the machining to be completed in a multi-dimensional space.

Although not wanting to be bound by theory, FIG. 1C describes the sequential physical mechanisms of laser base bone machining. For example, by providing a narrowly focused laser beam (170) on a bone sample will allow laser absorption by the bone tissue (172). The absorption of energy causes the instantaneous heat generation (174) within the bone tissue and the evaporation of a liquid layer and organic/inorganic bone components (176). A volatile destruction of bone matrix occurs due to an internal generation of rapid and high-value vapor pressure (178). The bone tissue residue ejection on vaporization occurs (180), wherein a micro-machined bone structure remains (182). This embodiment essentially comprises: a) observing a region of bone to be machined; b) calculating the temperature-dependent material properties of the region of bone; c) determining parameters for laser-assisted machining based on the temperature-dependent material properties of the region of bone; and d) performing laser-assisted bone machining using the determined parameters.

Figure 2B:
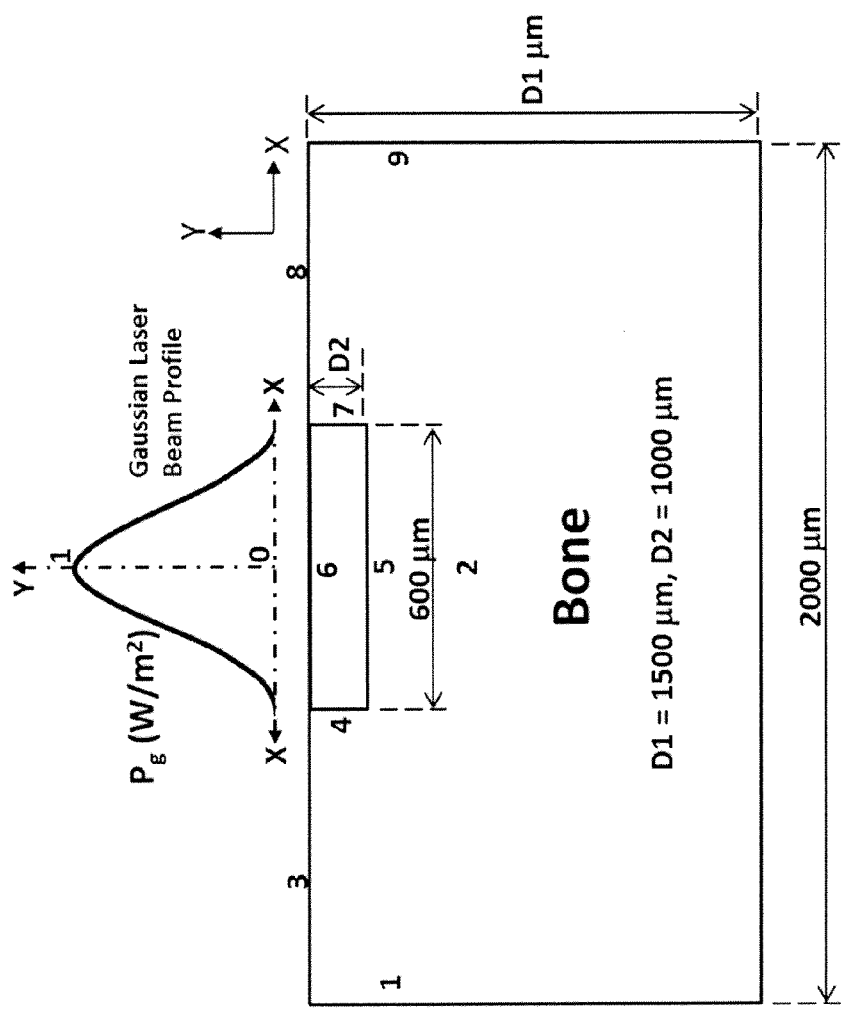
FIG. 2B shows the boundary conditions of computational model used in the present invention to represent the temperature-dependent material properties of a region of bone.

Although not wanting to be bound by theory, bone comprises ceramic/mineral components such as calcium phosphate and hydroxyapatite (HA); organic components such as collagen; and water. In order to provide governance to the process, a computational model of bone was developed. More specifically, FIG. 2A shows the computational model used to represent the temperature-dependent material properties for bone. The governing equations for the computational model are shown in Table 1 of FIG. 2A, with references directed to FIG. 2B.

Turning now to FIG. 2A and FIG. 2B. The boundary conditions for the whole geometry can be modeled using the governing equation:

$$\rho c_p \left[ \frac{\partial T}{\partial t} \right] = k \left[ \left( \frac{\partial^2 T}{\partial x^2} \right) + \left( \frac{\partial^2 T}{\partial y^2} \right) \right].$$

The boundary conditions for heat flux, natural convection cooling and radiation is represented in FIG. 2B, for area 6, has the model equation of:

$$-k\frac{\partial T}{\partial y} = \varphi P_g - h[T - T_i] - \varepsilon\sigma[T^4 - T_i^4]$$

where, $\phi=1$ for $0 \le t \le t_r$, and $\phi=0$ for $t \ge t_r$.

Additionally, the boundary conditions for the average laser power density in Gaussian distribution is represented in FIG. 2B, for area 6, has a the model equation of:

$$P_g = A\left[\frac{P}{\left(\frac{\pi}{4}D^2\right)}\right] \cdot \exp\left[-\left(\frac{(x-x_r)^2}{2\phi^2}\right)\right]$$

The boundary conditions for natural convection cooling and radiation in FIG. 2B, areas 1 and 9, has a model equation of:

$$-k\frac{\partial T}{\partial x} = h[T - T_i] - \varepsilon\sigma[T^4 - T_i^4]$$

The boundary conditions for natural convection cooling and radiation in FIG. 2B, areas 3 and 8, has a model equation of:

$$-k\frac{\partial T}{\partial y} = h[T - T_i] - \varepsilon\sigma[T^4 - T_i^4]$$

The boundary conditions for insulation in FIG. 2B, area 2, has a model equation of:

$$\frac{\partial T}{\partial y} = 0$$

Example 2

Machining Parameters

The distinct apparatus and sequential steps that were followed during present efforts in machining bone utilized the following laser: A diode pumped ytterbium (IPG YLS-3000) continuous wave fiber laser (1060-1070 nm wavelength) with Gaussian Beam of focal spot of 0.3 mm diameter was used at a fixed stand-off distance of 315 mm from the top surface of the sample for machining the bone (FIG. 1A). The bone sample (140) was tightly clamped (by using 3M double sided tape) on the copper plate (150). Nitrogen (30 liter/min with 35 psi pressure was used as an inert gas protection (120) of the bone sample from burning/charring at elevated temperature. Variable laser energy density (3-8.5×10$^6$ J/m$^2$ for different scanning speed (0.1-0.25 m/s) and residence time (i.e. 2-4 ms) were used to obtain adjustable bone machining rate of 3-65 m$^3$/s or 1-9×10$^{-2}$ m$^3$/s/W or M$^3$/J).

In specific embodiments, the process may utilizes one or more techniques to determine one or more characteristics of the bone to be machined, such as X-ray Computed Tomography (X-ray CT), Single Photon Emission CT (SPECT), Magnetic Resonance Imaging (MRI), Micro-Position Emission Tomography (microPET), Fluorescence Molecular Tomography (FMT), Mouse-Dual Energy X-ray Absorptiometry (DEXA), to determine the density (i.e. porosity) of the bone which in turn provides the estimate for total volume fraction of the components of bone (calcium phosphate-hydroxyapatite+collagen+and water) along with the estimates of elemental compositions and volume fractions of each of these bone components (calcium phosphate-hydroxyapatite, collagen, and water). Although not wanting to be bound by theory, knowing the thermo-physical properties such as thermal conductivity, specific heat, and density of each bone component from the literature, the thermo-physical properties of a given bone matrix (composite) may be computed. These thermo-physical properties, along with the dimensions of bone and boundary conditions are incorporated into the multiphysics based computational model of the present invention to predict the temperature-time history for machining a given bone. Although not wanting to be bound by theory, knowing this history, various laser parameters such as laser power and scanning speed may predicted to machine a given bone for required dimensions with the desired machining rate.

Bone's machined depth (d in µm) is a function of temperature (T in K):

$$d=f(T)$$

Temperature is a function of laser energy density (LED in J/m$^2$):

$$T=f(\text{LED})$$

Laser energy density is the function of laser power (P in W), beam focal spot diameter (diam. in m), and scanning speed (v in m/s):

$$\text{LED}=f(P,\text{diam},v)$$

The laser-assisted bone machining apparatus and process of the present invention exhibit several advantages over conventional technology. The present invention provides a chemically clean light source for machining. A coherent and monochromatic beam is delivered to the region to be machined, which provides narrow beams, high power density, and little or no heat affected zone ("HAZ") without physical contact and hence without mechanical loading and frictional forces. A flexible fiber optics beam allows for remote processing and is amenable to processing complex shapes quickly and easily. Finally, laser assisted machining (LAM) of bone integrated with a robotic-computer controller provides a highly precise method for machining complicated structural bones. The technique is also expected to facilitate rapid recovery with minimal traumatic injury, negligible heat-mark, and minimal invasive tissue damage that are typically associated with conventional orthopedic techniques.

Figure 3B:
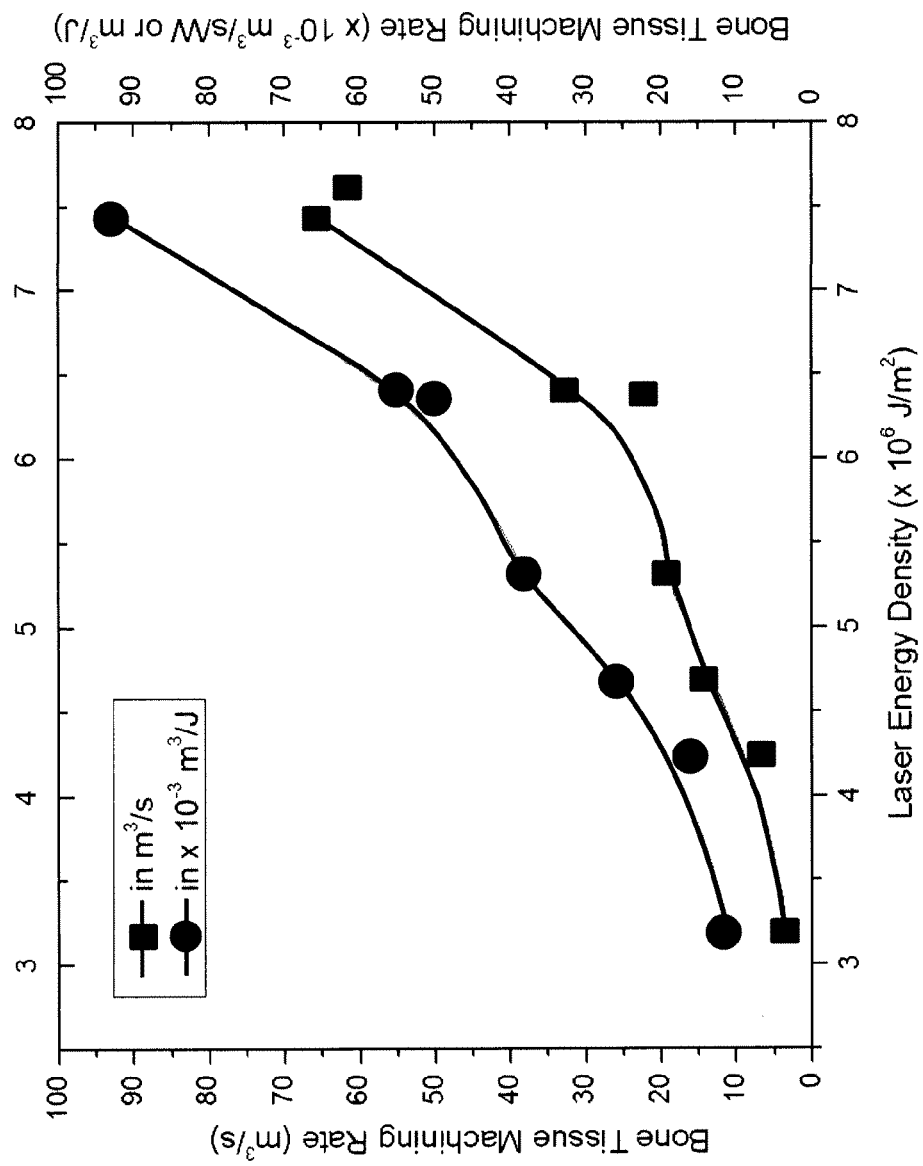
FIG. 3B shows a graphic representation of bone tissue machining rate as a function of laser energy density for the experiments carried out according to the present invention.
Figure 3C:
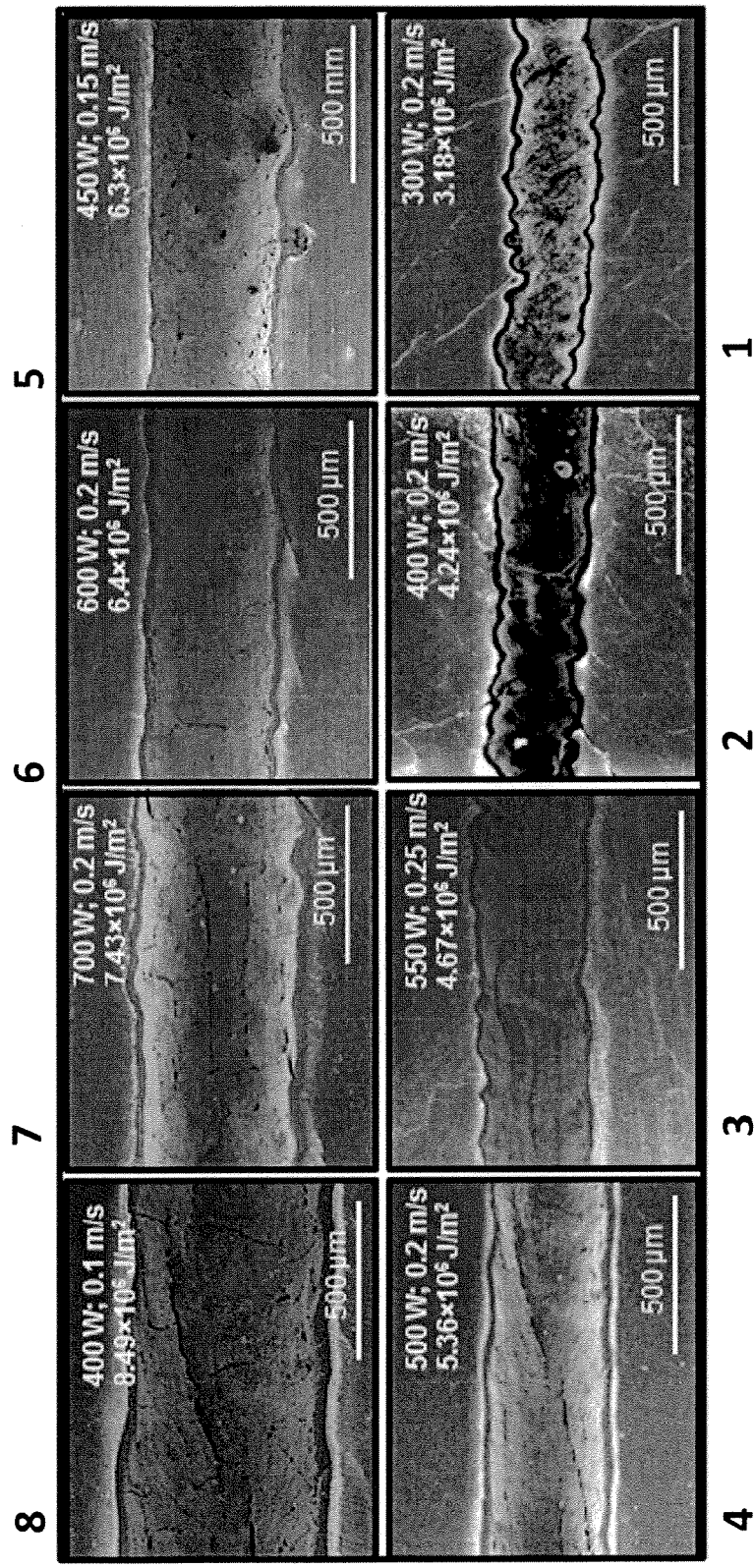
FIG. 3C shows scanning electron microscopy (SEM) surface views of the width of a laser based bone machined sample according to the present invention.
Figure 3D:
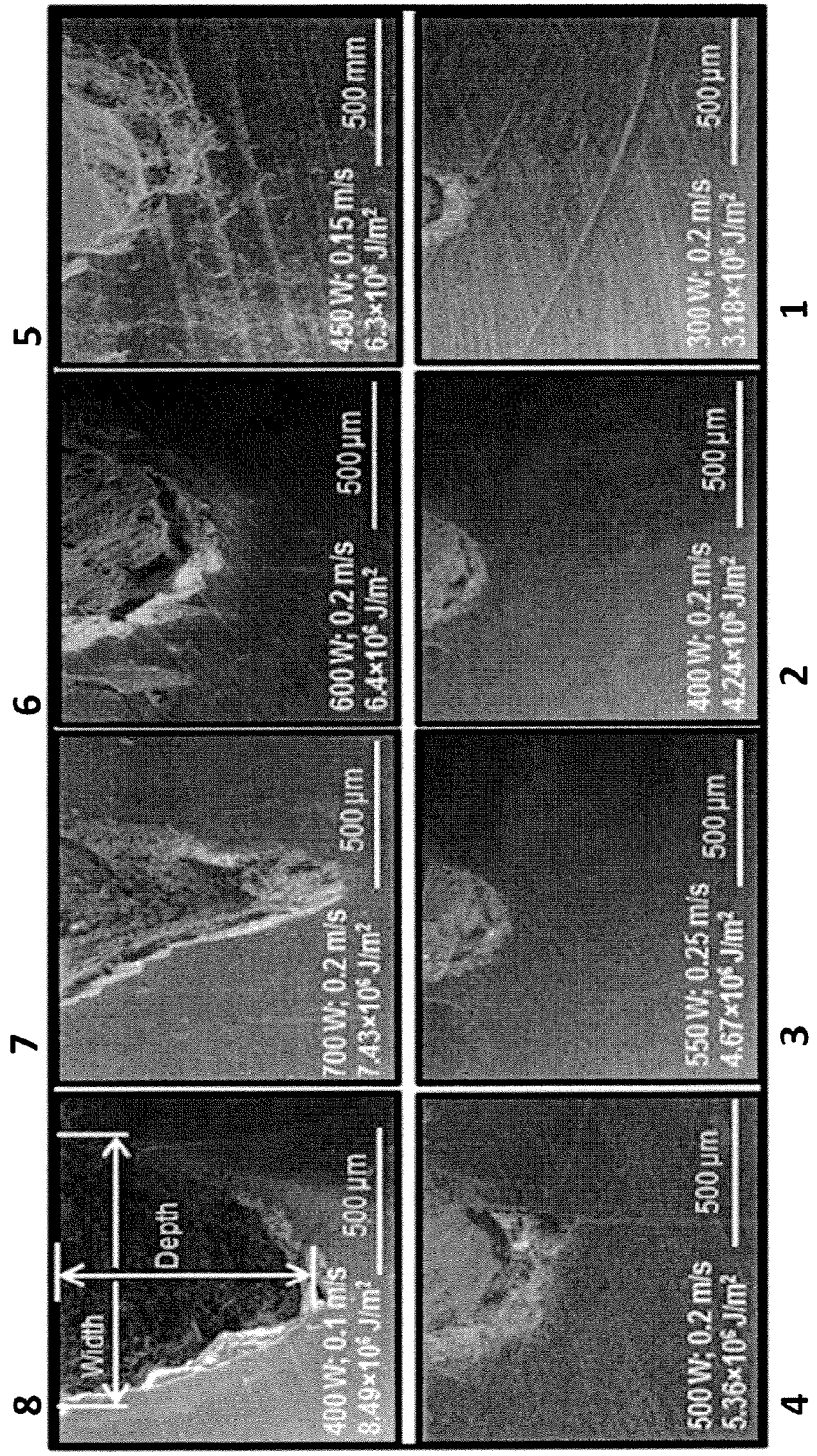
FIG. 3D shows SEM images of cross sectional views (i.e. width and depth) of laser-assisted bone machined samples in accordance with the present invention.

Turning now to FIG. 3A. The laser-assisted machining of bone was performed using eight different sets of parameters, wherein machining attributes and rates were measured. FIG. 3B shows bone tissue machining rate as a function of laser energy density for the experiments shown in FIG. 3A. FIG. 3C is an illustration showing the width of each of the eight parameters of FIG. 3A. In addition, FIG. 3D is an illustration showing the depth of each of the eight parameters of FIG. 3A. For example, the row of parameters listed in Experiment 1 of FIG. 3A indicate the following parameters: the laser power (W)=300 W; Scanning speed=0.2 m/s; Residence time=3.0 ms; Laser energy Density=3.18×10$^6$ J/giving a machining rate=3.3 m$^3$/s or a machining rate representing a volume of material removed (m$^3$)/residence time/laser energy density (J/m$^2$). The experimental width of bone cut using these parameters is shown in FIG. 3C (Panel 1). Similarly, the experimental depth of bone cut using these parameters is shown in FIG. 3D (Panel 1). The laser machining attributes of bone either measured computationally, or experimentally are compared in FIG. 3C.

Figure 4:
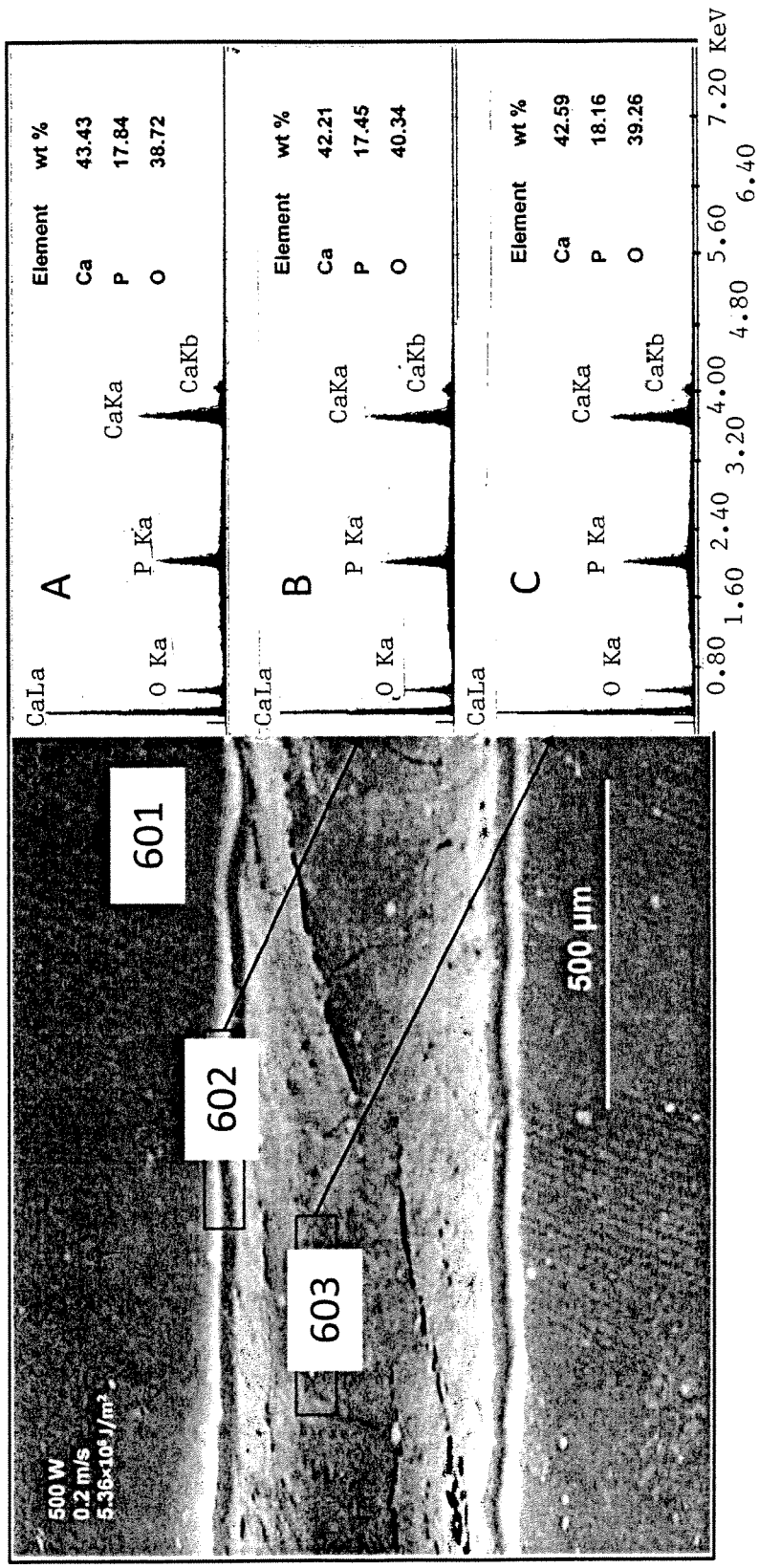
FIG. 4 shows an SEM view of laser machined bone sample at $5.36 \times 10^6$ J/m² laser energy density, showing several machined regions and the corresponding elemental composition within these regions. 601—base bone material; 602: heat affected zone surrounding machined region; and 603: machined bone region.

Turning now to FIG. 4, showing an illustration laser machined bone sample at $5.36 \times 10^6$ J/m² laser energy density. FIG. 4 shows several machined regions (601, 602, and 603) and the corresponding elemental composition within these regions (601—Panel A, 602—Panel B, and 603—Panel C). More specifically, Region 601 and Panel A correspond to the base bone material. Region 602 and Panel B correspond to the heat affected zone surrounding machined region. Region 603 and Panel C correspond to the machined bone area.

Figure 5:
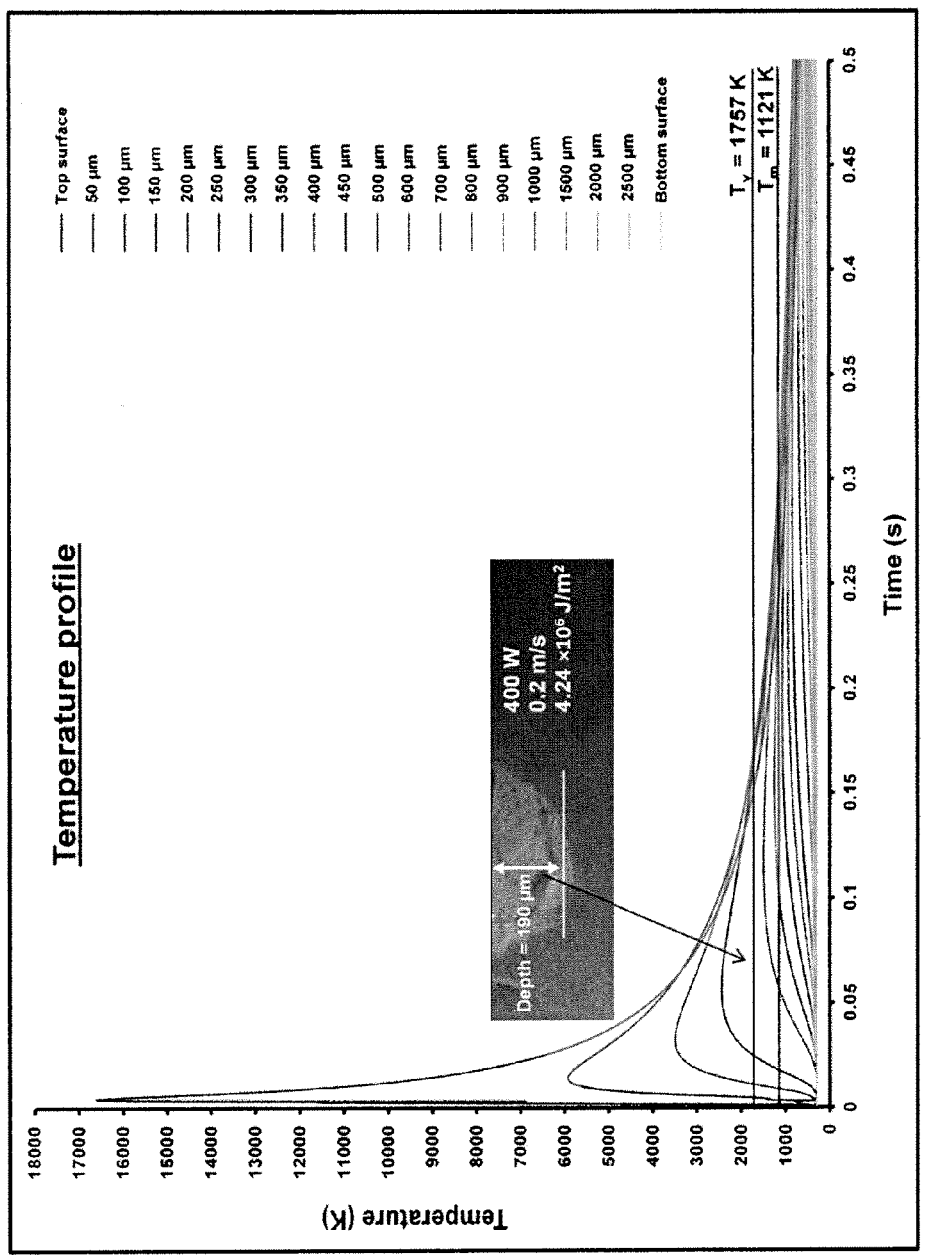
FIG. 5 shows temperature profiles at different depths for laser machined bone sample at $4.24 \times 10^6$ J/m², according to one process of the present invention.

In summary, when the highly focused laser beam was applied on the bone surface in shorter time scale (2-4 ms) due to laser absorption by bone tissue, the rapid generated heat intensity ($4.2$-$9.9 \times 10^7$ W/m²) was penetrated into the bone tissue that in turn created vapor pressure and plasma. The protruded plasma has further destructed the bone matrix deeply, which caused the ejection of residue of machined bone tissue. Depending on the applied laser energy density (combination of laser power, laser beam traverse speed and beam size on the bone surface) and corresponding cooling rate, various levels of volume of bone removal and corresponding bone machining rate can be achieved with minimal or not heat affected zone surrounding the machined region. Furthermore, such a combination of machining parameters raise the temperature within the laser beam-bone interaction region at the level (FIG. 5) that machines the bone without damaging the tissues in the regions surrounding the machined area (FIG. 4). Such carefully selected laser machining parameters also allow preserving the composition of bone tissue within the machined regions same as the surrounding region and the base bone material (FIG. 4—Panels A-C).

Example 3

LAM of Bone with Computer Numeric Controlled Robotics

Figure 6:
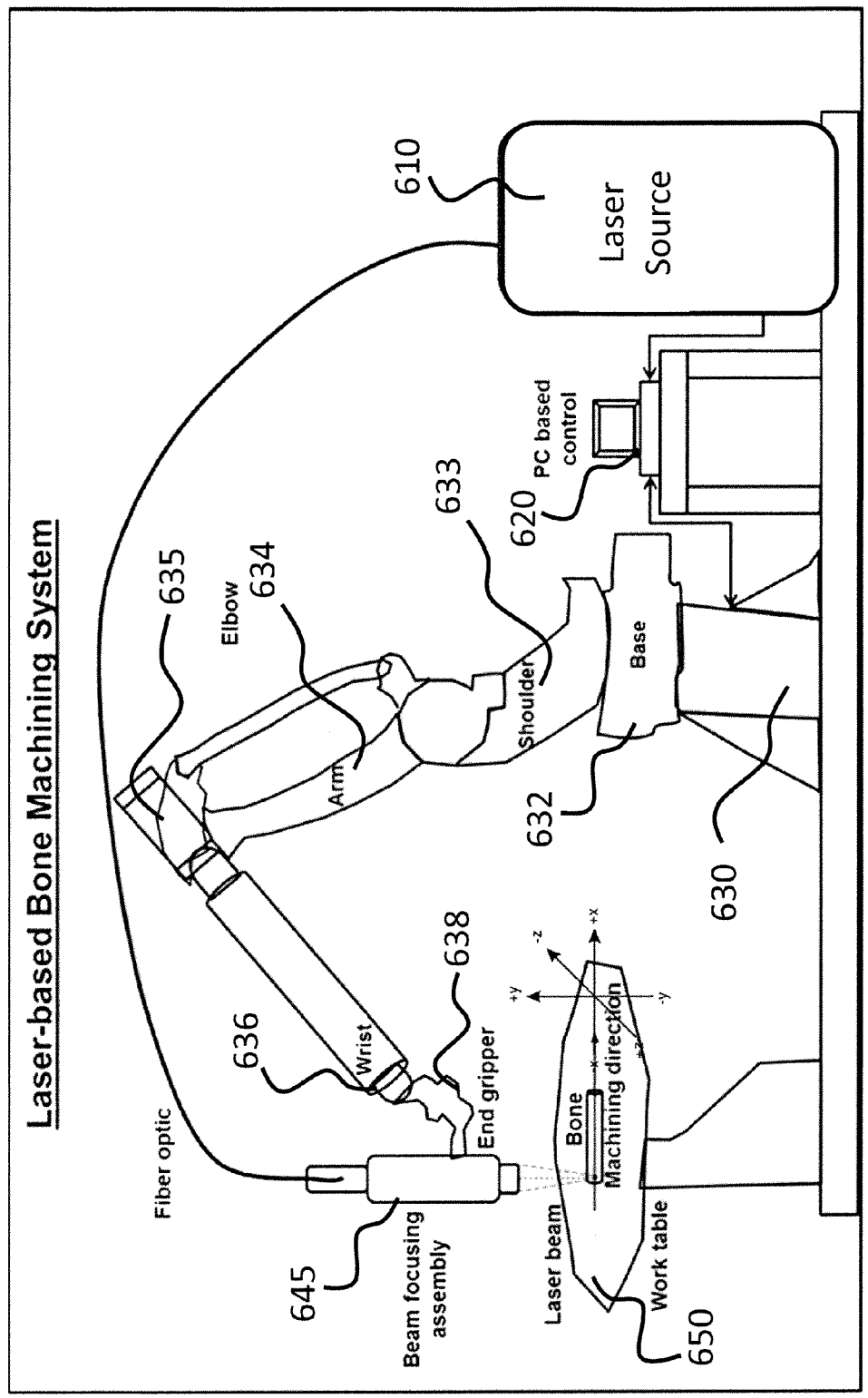
FIG. 6 shows an automated computer numeric controlled ("CNC") bone machining system, in an embodiment of the present invention.

The uniqueness of the current invention with regard to the elements shown FIG. 6, which represents an automated bone milling system. More specifically, both hard tissues and bones are composed of multiple components such as organic (calogen), inorganic (calcium phosphate) and water that in turn exist in various volume fractions and physical formats. These components have different thermo-physical properties. Hence, in order to machine these tissues in complex configurations with high accuracy and speed without damaging the surrounding tissues, the laser parameters (power, scan speed, beam focus) and motion system (robot) parameters (speed and position) required to be synchronized and controlled accurately/precisely. This is possible through the control and synchronization of the general elements of the milling system depicted in FIG. 6.

Turning now to FIG. 6, a laser source (610) is in fiber optical connection with the beam focusing assembly (645). The laser source is also in electrical communication with a controller device, in this case it is a computer (620). The computer is also in electrical communication with the robotic arm. The robot sits on a stand (630), having a base (632) that is in mechanical and electrical communication with the shoulder (633), the arm (634), the elbow (635), the wrist (636) and the end gripper (638). The end gripper of the robotic arm (638) is attached to the beam focusing assembly (645) and can be controlled using the computer (620). A bone sample (641) located on the work table (650) can be machined using the automated robot arm integrated with the laser source.

The technique is a non-contact simple procedure this is also a flexible method. The laser beam can be delivered via fiber optic to the bone that is being machined. Such a laser beam delivery can be achieved with either a manually operated hand held devices or by a computer numeric controlled ("CNC") robotic system for full automations (FIG. 6). In both cases, the vision system can be integrated with the beam delivery system for beam guidance during machining simple as well as complex profiles. Due to the fiber optic delivery based approach, the laser can be situated and operated remotely. Both, laser operation (for power adjustment) and beam motion system, if it is fully robot based, can be computer numeric controlled for height precision. Furthermore, the envelope for operating parameters and the types of tissue materials (hard and soft) that can be handled (machined) can be extended employing various types of lasers (infrared and ultraviolet wavelength range (See FIG. 7) in both manual, semi-automated and fully automated machining operations'

The present invention provides a process for laser-assisted bone machining. In one embodiment, the process comprises the steps of: a) providing a focused laser beam; b) laser absorption by tissue; c) instantaneous heat generation; d) evaporation of a liquid layer and organic/inorganic components of the bone; e) volatile destruction of bone matrix by internal generation of rapid and high-value vapor pressure; and f) tissue residue ejection and vaporization, resulting in micro-machined bone structure.

REFERENCES CITED

The following references, to the extent that they provide exemplary procedural or other details supplementary to those set forth herein, are specifically incorporated herein by reference.

US PATENT DOCUMENTS

US Patent Publication No. 2011/0218524 A1, published on Sep. 8, 2011, with Giorgio Cattaneo listed as the inventor.

NON-PATENT LITERATURE

S. Santhanakrishnan, Y. H. Ho, and N. B. Dahotre, Laser coating of hydroxyapatite on Mg for enhanced physiological corrosion resistance and biodegradability, Materials Technology (2012) 1-5.

J. P. Winkler, The temperature study of laser-irradiated bone, Dissertation for Doctor of Philosophy, The University of Tennessee, Knoxille, Tenn. (1997) 1-86.

K. J. Altman, Microscale machining and mechanical characterization of bone tissue, Thesis for Master of Science, The Ohio State University, Columbus, Ohio (2009) 1-105.

M. Ivanenko, M. Werner, S. Afilal, M. Klasing, P. Hering, Ablation of bone tissue with pulsed $CO_2$ lasers, Medical Laser Application 20 (2005) 13-23.

A. B. Imhoff, The use of lasers in orthopaedic surgery, Operative Techniques in Orthopaedics 5 (1995) 192-203.

J. Burgner, M. Mueller, Robot assisted laser bone processing: Marking and cutting experiments, International Conference on Advanced Robotics (ICAR 2009), 22-26 Jun. 2009, 1-6.

J. M. White, D. Gekelman, J. Budd, Lasers and dental soft tissues: Reflections on our years of research, International Congress Series 1248 (2003) 13-19.

R. J. Wallace, C. J. Whiners, J. A. McGeough, A. Muir, Experimental evaluation of laser cutting of bone, Journal of Materials Processing Technology 149 (2004) 557-1560.

J. L. Fox, The use of laser radiation as a surgical "light knife," Journal of Surgical Research 9 (1969) 199-205.

J. D. B. Featherstone, D. Fried, Fundamental interactions of lasers with dental hard tissues, Medical Laser Application 16 (2001) 181-194.

F. W. Neukam, F. Stelzle, Laser tumor treatment in oral and maxillofacial surgery, Physics Procedia 5 (2010) 91-100.

B. L. Yilbas, Z. Yilbas, M. Sami, Thermal processes taking place in the bone during $CO_2$ laser irradiation, Optics & Laser Technology 28 (1996) 513-519.

S. Karmani, The thermal properties of bone and the effects of surgical intervention, Current Orthopaedics 20 (2006), 52-58.

Katrina J. Altman, Microscale Machining and Mechanical Characterization of Bone Tissue, Master of Science Thesis, Ohio State University, 2009.

What is claimed is:

1. A method of laser-assisted machining of a bone, comprising the steps of:
   a) determining a target bone volume to be machined;
   b) calculating a temperature-dependent material properties of the target bone volume to be machined;
   c) scanning a focused laser beam along a surface area axis of the target bone volume at a machining rate; and
   d) ejecting a bone residue from the determined target bone volume creating a machined void in the bone;
   wherein the machining rate is determined from a laser power output, the target bone volume, a diameter of the focused laser beam, a laser scanning speed, a residence time, and a laser energy density (LED); and wherein the focused laser beam provides a narrow beam with a high power density and having low heat affected zones on the target bone volume; and wherein a governing equation for a whole geometry boundary conditions of the target bone volume is:

$$\rho c_p \left[\frac{\partial T}{\partial t}\right] = k\left[\left(\frac{\partial^2 T}{\partial x^2}\right) + \left(\frac{\partial^2 T}{\partial y^2}\right)\right]$$

wherein, x is an X-coordinate in a three dimensional space (m); y is a Y-coordinate in a three dimensional space (m); $\rho$ is Density (kg/m$^3$); $C_p$ is specific heat at constant pressure (J/kg·K); T is Temperature (K, Kelvin); t is Time (s, seconds) and k is thermal conductivity (W/m·K).

2. The method of claim 1, further comprising the step of: defining a Gaussian laser beam profile for the target bone volume to be machined.

3. The method of claim 1, further comprising the step of: defining a top-hat laser beam profile for the target bone volume to be machined.

4. The method of claim 1, further comprising the step of: choosing the laser to generate the focused laser beam having the laser energy density in the range of 2.0 to 12.0×10$^6$ J/m$^2$.

5. The method of claim 3, further comprising the step of: choosing the laser to generate a focused laser beam having a wavelength in the range of 300 nm to 10,600 nm.

6. The method of claim 3, further comprising the step of: choosing the laser to generate a focused laser beam from: a Ti-Sapphire laser, a $CO_2$ laser, a Excimer laser, a YAG laser, or combination thereof.

7. The method of claim 3, further comprising the step of: choosing the laser to generate the focused laser beam to be a diode-pumped ytterbium (PG-YLS-3000) continuous wave fiber laser having a 1060 nm-1079 nm wavelength with a Gaussian or top-hat beam of focal spot of 0.3 mm diameter used at a fixed stand-off distance of 315 mm from the surface area axis.

8. The method of claim 1, further comprising the step of: integrating a vision system and a computer numeric controlled ("CNC") robotic system to the laser for full automation of selecting the target bone volume scanning the focused laser beam along a surface area axis of the target bone volume at a machining rate.

9. The method of claim 1, further comprising the step of: setting the residence time of the laser to be in the range of 2-4 ms when the focused laser beam is generating a heat intensity in the range of 4.2-9.9×10$^7$ W/m$^2$.

10. A process for laser-assisted machining comprising the steps of:
    a) observing a region of bone to be machined;
    b) calculating the temperature-dependent material properties of the region of bone;
    c) determining parameters for laser-assisted machining based on the temperature-dependent material properties of the region of bone; and
    d) performing laser-assisted bone machining using the determined parameters;
    wherein a governing equation for a whole geometry boundary conditions of the region is:

$$\rho c_p \left[\frac{\partial T}{\partial t}\right] = k\left[\left(\frac{\partial^2 T}{\partial x^2}\right) + \left(\frac{\partial^2 T}{\partial y^2}\right)\right]$$

wherein, x is an X-coordinate in a three dimensional space (m); y is a Y-coordinate in a three dimensional space (m); $\rho$ is Density (kg/m$^3$); $C_p$ is specific heat at constant pressure (J/kg·K); T is Temperature (K, Kelvin); t is Time (s, seconds) and k is thermal conductivity (W/m·K).

11. An apparatus for machining bone, comprising:
    a) a laser source capable of delivering a focused laser beam with a Gaussian or top-hat laser beam profile;
    b) a dynamic focusing unit for delivering the focused laser beam to a visualized target site;
    c) a real time controller (RTC) capable of simultaneous processing of visualized target site data and controlling the laser source and controlling the dynamic focusing unit;
    wherein the RTC is able to correct laser source output for the purpose of preventing heat affected zones in the bone target and machining bone in a predetermined pattern;
    wherein a governing equation for a whole geometry boundary conditions of the region is:

$$\rho c_p \left[\frac{\partial T}{\partial t}\right] = k\left[\left(\frac{\partial^2 T}{\partial x^2}\right) + \left(\frac{\partial^2 T}{\partial y^2}\right)\right]$$

wherein, x is an X-coordinate in a three dimensional space (m); y is a Y-coordinate in a three dimensional space (m); $\rho$ is Density (kg/m$^3$); $C_p$ is specific heat at constant pressure (J/kg·K); T is Temperature (K, Kelvin); t is Time (s, seconds) and k is thermal conductivity (W/m·K).

12. The apparatus of claim 11, wherein the laser source delivers a beam having a 1060 nm-1079 nm wavelength with a Gaussian or top-hat beam of focal spot of 0.3 mm diameter.

13. The apparatus of claim 11, wherein the laser comprises a diode-pumped ytterbium (PG-YLS-3000) continuous wave fiber laser having a 1060-1079 nm wavelength with a Gaussian or top-hat beam of focal spot of 0.3 mm diameter used at a fixed stand-off distance of 315 mm from the surface area axis.

14. The apparatus of claim 11, wherein the focused laser beam has a laser energy density in the range of 2.0 to $12.0 \times 10^6$ $J/m^2$.

15. The apparatus of claim 11, wherein the focused laser beam has a wavelength in the range of 300 nm to 10,600 nm.

16. The apparatus of claim 11, wherein the laser comprises a Ti-Sapphire laser, a $CO_2$ laser, a Excimer laser, or a YAG laser.

17. The apparatus method of claim 11, further comprising a computer numeric controlled ("CNC") robotic system to enable the laser to have full automation of selecting a target bone volume and scanning the focused laser beam along a surface area axis at a determined machining rate.

18. The apparatus of claim 11, further comprising the laser having a resident time the range of 2-4 ms when the focused laser beam is generating a heat intensity in the range of $4.2\text{-}9.9 \times 10^7$ $W/m^2$.

* * * * *